United States Patent [19]

Ivy

[11] 4,218,651
[45] Aug. 19, 1980

[54] APPARATUS FOR DETECTING LONGITUDINAL AND TRANSVERSE IMPERFECTIONS IN ELONGATED FERROUS WORKPIECES

[76] Inventor: Leon H. Ivy, Box 1325, Alvin, Tex. 77511

[21] Appl. No.: 930,131

[22] Filed: Aug. 2, 1978

Related U.S. Application Data

[63] Continuation of Ser. No. 786,689, Apr. 11, 1977, abandoned, which is a continuation of Ser. No. 599,177, Jul. 25, 1975, abandoned.

[51] Int. Cl.² .................... G01R 33/12; G01R 1/04
[52] U.S. Cl. ............................ 324/227; 324/242; 324/151 R
[58] Field of Search .............. 324/227, 232, 240, 242, 324/151 R, 97, 154 R

[56] References Cited

U.S. PATENT DOCUMENTS

| | | | |
|---|---|---|---|
| 2,031,469 | 2/1936 | Drake | 342/227 |
| 2,211,017 | 8/1940 | Leifer, et al. | 324/224 |
| 2,435,985 | 2/1948 | Stewart et al. | 324/240 |
| 2,495,627 | 1/1950 | Bovey | 342/234 |
| 3,056,081 | 9/1962 | Hochschild | 324/238 |
| 3,535,624 | 10/1970 | Wood | 324/226 |
| 3,786,684 | 1/1974 | Wiers et al. | 324/220 |
| 3,899,734 | 8/1975 | Beaver et al. | 324/220 |
| 3,906,357 | 9/1975 | Runshang | 324/226 |

Primary Examiner—Rudolph V. Rolinec
Assistant Examiner—Walter E. Snow
Attorney, Agent, or Firm—Bard & Groves

[57] ABSTRACT

Apparatus for detecting defects such as fissures in the ferrous metal of elongated workpieces such as pipe may take the form of wall thickness and material continuity inspection apparatus that is located at an inspection site, with the inspection site being provided to receive an elongated metal workpiece such as a section of drill stem. A movable magnet support structure is located at the inspection site and carries a magnet and coil assembly in movable shoe means that is capable of engaging the outer periphery of the workpiece and establishing a predetermined spaced relationship between the workpiece, the magnet and the coil. The magnet support shoe, together with the magnet and coil, are movable in helical manner about the workpiece, causing the shoe to traverse the entire outer periphery of the workpiece during a single inspection pass. The magnet is arranged to generate a small localized elongated magnetic field within the workpiece, which elongated field is oriented with respect to the longitudinal axis of the workpiece with the lines of flux of the magnetic field being transversely oriented with respect to the longitudinal axis of the workpiece. Thus oriented, the magnetic field enables electronic detection of longitudinal fissures in the workpiece as it traverses the length of the workpiece. An electric current is induced in the coil, which is oriented substantially 90° to the flux of the magnetic field, and modifications in the flux, and thus the current induced in the coil, are detected and relayed to suitable electronic equipment for amplification and display in any suitable manner. A second magnet and coil assembly provided by movable magnet and coil-carrying shoes may be provided having transversely oriented elongated magnetic field means with the lines of flux of the magnetic field means defining planes that are parallel with the longitudinal axis of the workpiece. The transversely oriented elongated magnetic field means are provided for the purpose of detecting transverse flaws or imperfections in the workpiece during the same inspection pass. An induction process is also provided for detecting variations in wall thickness of the workpiece being inspected.

3 Claims, 18 Drawing Figures

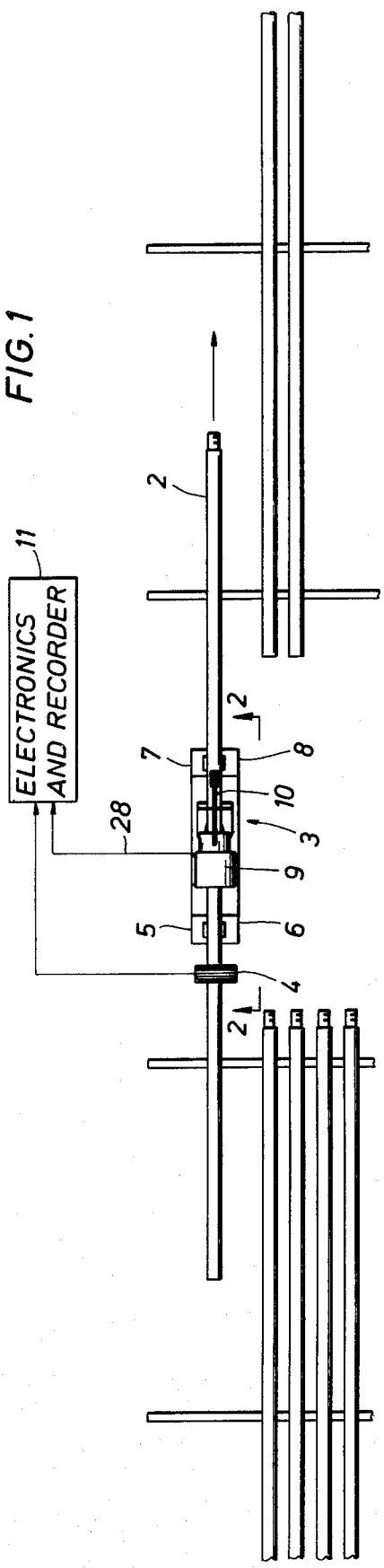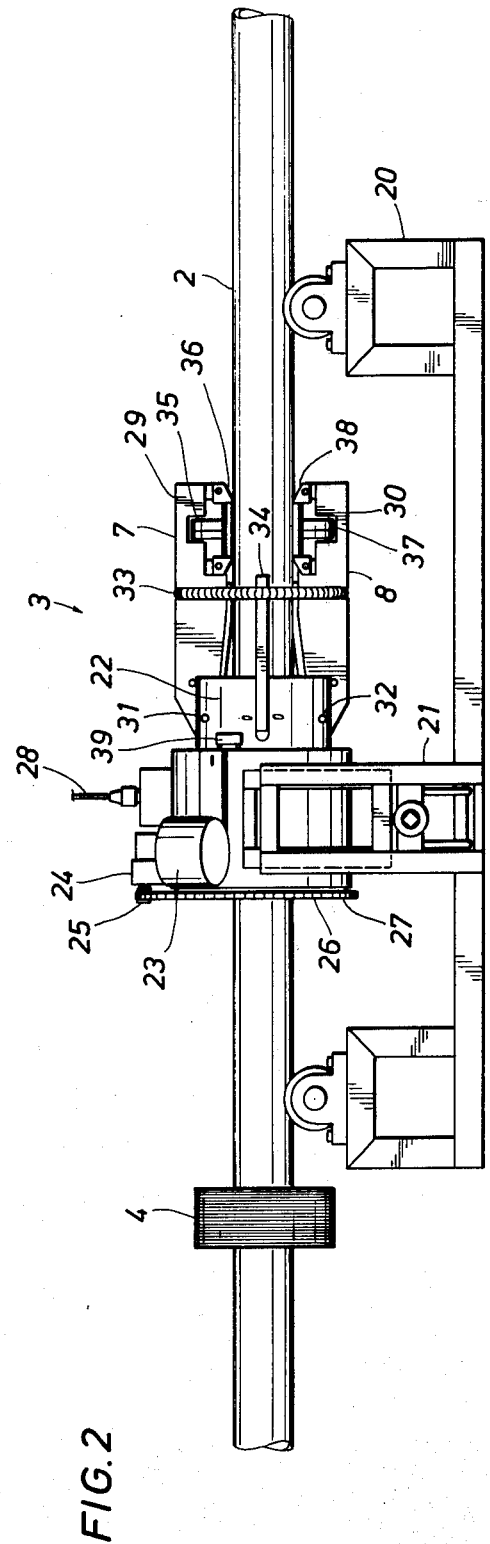

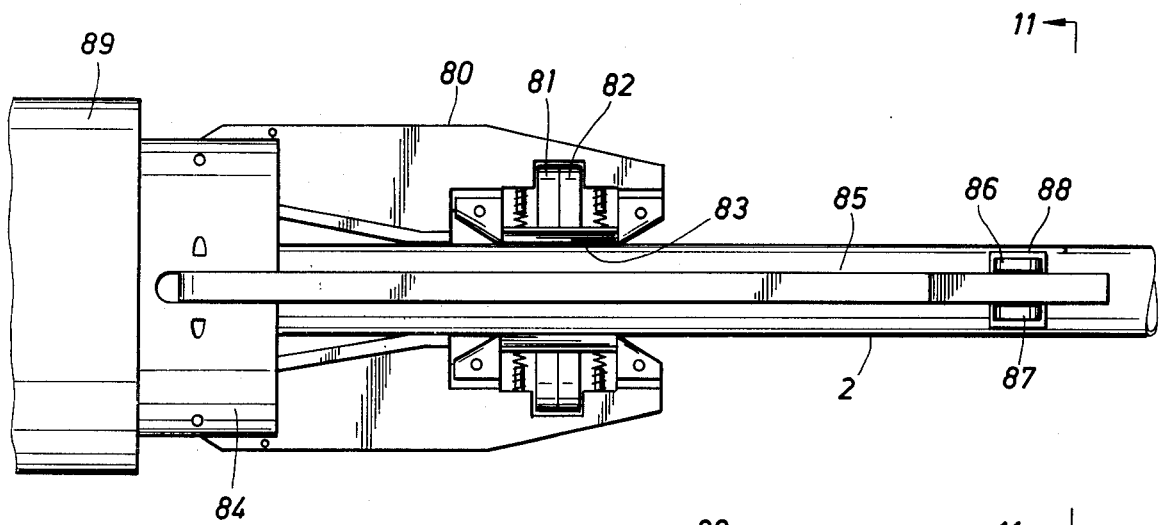
FIG. 10
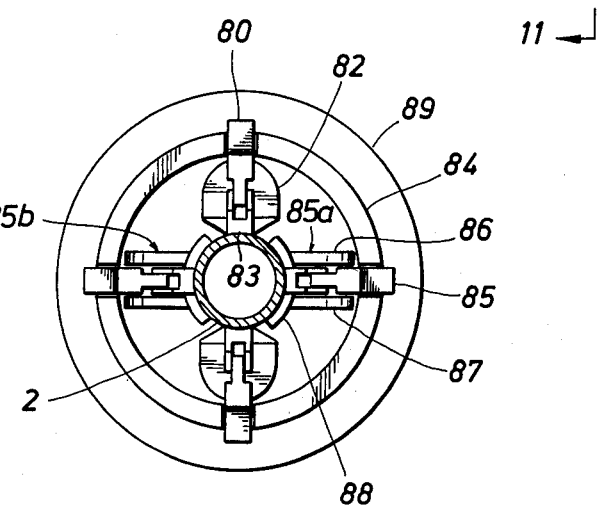
FIG. 11
FIG. 12
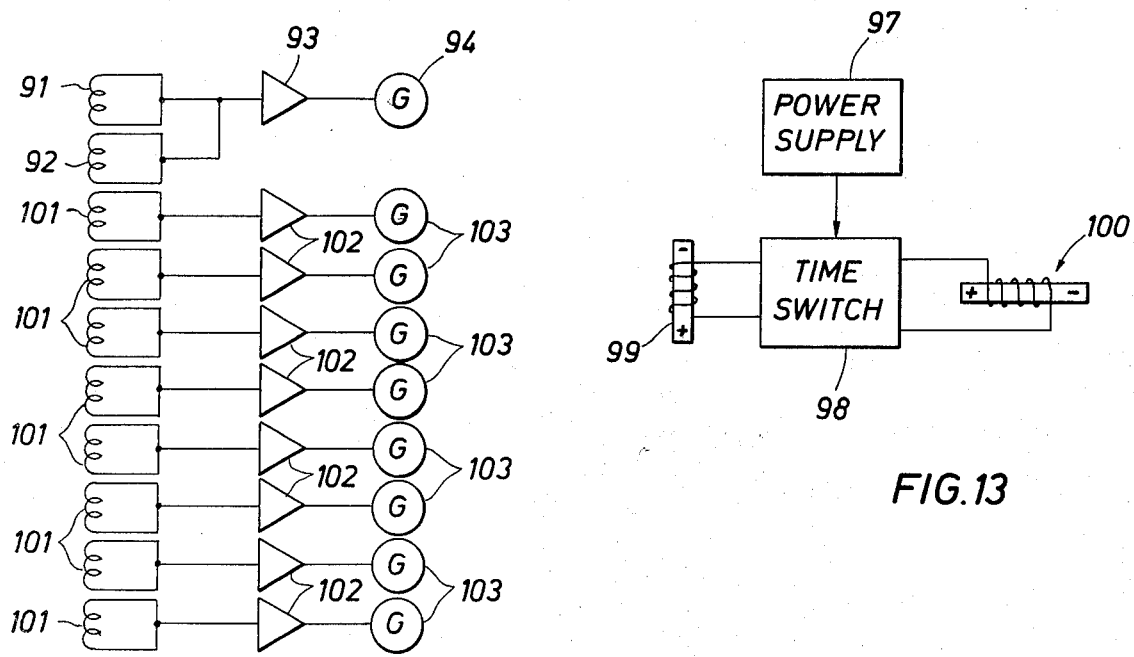
FIG. 13

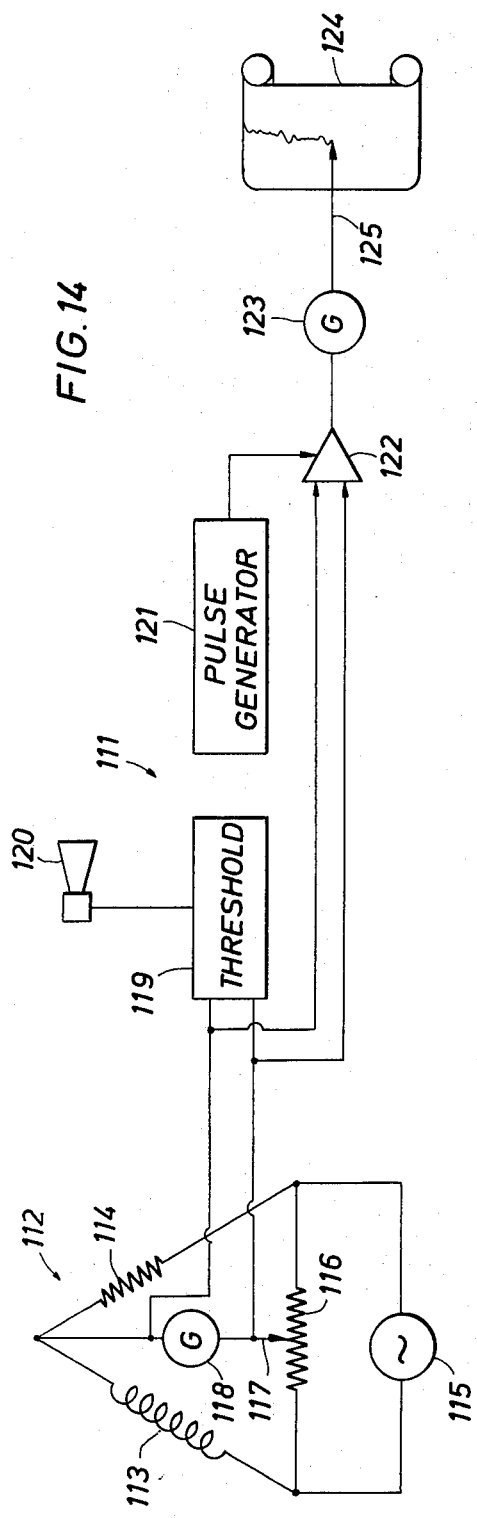
FIG.14
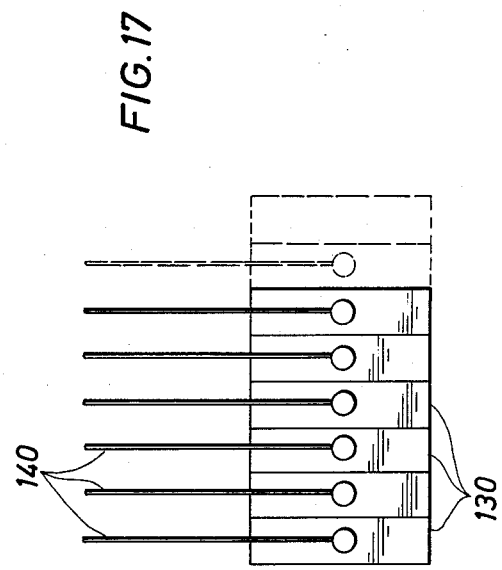
FIG.17
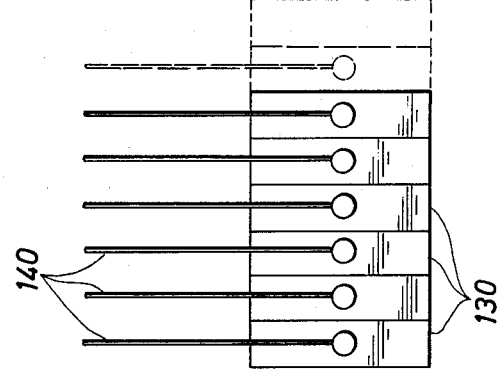
FIG.16
FIG.15

APPARATUS FOR DETECTING LONGITUDINAL AND TRANSVERSE IMPERFECTIONS IN ELONGATED FERROUS WORKPIECES

Related Applications

This application is a continuation of U.S. Ser. No. 786,689, filed Apr. 11, 1977, which is in turn a continuation of U.S. Ser. No. 599,177, filed July 25, 1975, both of which are now abandoned.

FIELD OF THE INVENTION

This invention relates generally to non-destructive testing of metal workpieces and more particularly relates to the testing of elongated workpieces such as drill stem for detection of fissures and other imperfections in the metal of the workpiece and identifies the fissure or imperfection as being of longitudinal or transverse nature relative to the elongated axis of the workpiece. The invention also provides for non-destructive detection of any variations in the thickness and hardness of the workpiece.

BACKGROUND OF THE INVENTION

Steel tubing is widely used in the petroleum industry for production of oil and gas from subsurface well formations that are typically located many hundreds or thousands of feet below the surface of the earth. The tubing must be supported at its upper extremity, and therefore it is necessary that each section of the tubing string be capable of supporting the entire weight of the string of tubing connected below it. The tension stresses that are placed on the tubing can cause either partial or total rupture of the tubing in the event the tubing was either manufactured with a fissure or flaw in the wall section thereof or if the tubing might have developed a stress crack while in use. For example, the tubing manufacturing process might have caused a section of tubing to be manufactured with a small fissure in its wall structure. When this tubing becomes highly stressed as it supports the weight of the tubing string below it, the small imperfection might open up to the point that leakage occurs. In this event, it is necessary to pull the tubing string and replace the defective tubing section, and logically this is a very expensive procedure that should be avoided if at all possible. As another example, steel tubing that is supported within a well where the production fluid being produced has a high concentration of hydrogen sulfide can cause hydrogen sulfide embrittlement of the tubing to occur, developing minute cracks that in time will begin to leak or cause separation of the tubing. If tubing has been utilized in a well having a high concentration of hydrogen sulfide, it may pass pressure and stress tests. However, when inspected by magnetic detection, otherwise undetectable fissures or subsurface flaws may be detected that will cause the tubing to be rejected for further use.

Drill stem and other pipe may be tested in the same manner to indicate any longitudinal or transverse imperfections in the material from which it is composed. Detection of otherwise undetectable flaws in the structure of drill stem or other pipe can, of course, prevent costly interruptions in drilling or production that render magnetic detection of such flaws extremely advantageous.

The theory of a "longitudinal defect" in metal tubing or pipe is that it creates in effect a single metal bar that is bent around the axis of the pipe. When the pipe is subjected to a magnetic field of constant strength and polarity, the "bar" becomes magnetized, whereby each side of the defect is at a different polarity. It is well known in the art to utilize this concept by passing a coil over a defect in a pipe at a constant speed, thereby cutting the magnetic lines of force in the coil to induce an electromotive force (EMF) into the coil proportional to the magnetic field in the defect. This EMF is of course detected and measured to detect the defect, per se, in non-destructive testing apparatus that is presently being utilized in the industry.

One of the problems with the magnetic detection technique in the prior art is that all parameters must be held constant from point to point (or else known), or else the EMF cannot provide a reliable indication of the size of the defect. For example, two consecutive points may have different magnetisms, whereby the respective EMF thereof will be different—even when the two defects are of the same size and characteristic. Moreover, magnetic testing utilizing single "bar" technique is not typically of such sensitivity that very small surface or subsurface fissures can be detected with a high degree of accuracy. It is desirable, of course, to provide non-destructive testing equipment having the capability of detecting metal flaws of any size or characteristic so as to eliminate the possibility of placing any tubing in service that might rupture under pressure or mechanical stress or develop leakage.

Many techniques have been proposed for overcoming this disadvantage in the prior art. For example, some devices provide for rotating either the pipe within the coil or, in the alternative, rotating the coil about the pipe in order to produce a more uniform and therefor constant magnetizing of the pipe. Alternatively, additional magnets producing lines of flux that are oriented at 90° to the direction of the coil are often used to greatly intensify magnetization, whereby the relatively small natural or residual magnetism in the pipe is overridden and swamped. This, in turn, has greatly enlarged and complicated the non-destructive testing equipment.

Wall thickness testing for pipe and tubing is generally accomplished in accordance with the eddy current concept with a pair of spaced coils about the workpiece being energized to induce a magnetic field into the workpiece, and with an intermediate coil between them to pick up any changes in the magnetic field. The fact that the magnetic fields are not induced into the workpiece at the point of a defect but rather remote to it causes this type of testing to be fairly inaccurate.

It is therefore a primary feature of the present invention to provide novel non-destructive testing equipment utilizing the magnetization concept but overcoming the problems that are generally associated with the "magnet bar" concept that is presently employed for non-destructive testing of metal pipe and tubing.

It is also a feature of the present invention to provide novel, non-destructive testing apparatus wherein a small amount of flux is located at the precise location of any defect and is generally oriented in a coinciding manner relative to the defect in order that the defect may be more readily observed.

An even further feature of the present invention contemplates the provision of novel non-destructive testing apparatus for elongated metal objects such as tubing and pipe wherein a magnetic field is generated in the metal object that is extremely small relative to the object as a whole but is very large in relation to the amount of residual magnetism at the defect, per se, thereby causing even a minute defect to produce a rather substantial change in the electronic detection signal, thereby giving a more strong indication of the presence of a defect than is otherwise obtainable.

It is also an important feature of the present invention to provide novel, non-destructive testing apparatus utilizing the magnet and coil detection concept wherein substantially greater penetration of the magnetic field is achieved relative to the metal object being inspected, thus enhancing accuracy of the testing process and providing a more positive indication of the defect than is otherwise typically obtainable.

It is an even further feature of the present invention to provide novel, non-destructive testing apparatus that promotes a general reduction in the overall size of the magnetic testing equipment without in any way detracting from the quality of flaw detection that is available through use of such equipment.

Another important feature of the present invention contemplates the provision of novel testing apparatus for inducing a magnetic field into the workpiece being inspected and moving the magnetic field along the length of the workpiece and for detecting dimensional changes in the thickness of the workpiece by monitoring electrical signals relating to the magnetic field.

Other and further features and advantages of the invention will become obvious to one skilled in the art upon an understanding of the illustrative embodiment about to be described, and various advantages not referred to herein will occur to one skilled in the art upon employment of the invention in practice.

SUMMARY OF THE INVENTION

In accordance with the present invention, an inspection site is provided having means for transporting an elongated workpiece such as a section of tubing, drill pipe or the like in a generally horizontal manner. A housing or other support structure is located at the inspection site and is capable of inspecting the workpieces as they are moved in generally parallel manner to a horizontally oriented path or axis. A single linear inspection pass of the workpiece along the inspection axis causes testing of the workpiece for longitudinal and transverse cracks or flaws in the metal of the workpiece and inspects the workpieces for dimensional changes in the body wall structure thereof. A first magnet support head is carried by the housing and is rotatable about the workpiece such that magnet support head structure carried by the rotatable head will move in helical manner relative to the moving workpiece in order to cause magnetic detection apparatus supported thereby to traverse the entire peripheral surface of the workpiece during a single inspection pass. Where tubing is being inspected, the apparatus may be employed to inspect it from the outside or inside as desired. A tool may be passed through the tubing of a well, for example, to test the tubing in place for structural continuity and wall thickness.

In one form of the invention, at least one, and preferably a pair, of movable magnet shoe elements are supported by the rotatable head and are capable of engaging the outer periphery of the workpiece at all times during the inspection pass. Movement of the magnet support shoe assemblies allows inspection contact to be maintained with the workpiece, even though the outer periphery of the workpiece may have changes in its dimension throughout its length.

Each of the magnet support shoe assemblies is of elongated nature and is positioned in substantially parallel relationship with the axis of the workpiece being tested for longitudinal flaws. The magnet support shoe provides support for a generally horseshoe-shaped electro-magnet or permanent magnet having each of its extremities directed toward the workpiece and being slightly spaced from the workpiece by a wear-resistant core that has engagement with the workpiece during the inspection movement. The magnetic field of the magnet is spread to an elongated form by pole pieces at each of the legs thereof. The wear-resistant core, which may be composed of non-magnetic metal or plastic material, contains an electrical coil that is positioned within the magnetic field of the magnet and has induced therein an electromotive force (EMF) by the magnet. The EMF induced into the coil is transmitted to appropriate amplification and signal display equipment by electrical circuitry that is connected to the coil.

With the magnet or magnets, as the case may be, located transversely to the longitudinal axis of the workpiece being tested, a small, localized but elongated magnetic field is developed in a portion of the workpiece having the lines of flux of the magnetic field being substantially normal to the longitudinal axis of the workpiece and to the coil. The magnetic field takes on a particular characteristic as long as the material of the workpiece is free of flaws. When the magnetic field within the metal of the workpiece is traversed by or traverses a flaw in the workpiece, the small localized magnetic field is severely distorted, and this distortion is communicated to the coil by virtue of the change in the lines of flux being interrupted by the coil. Differentiation between the electronic signal being transmitted by the undisturbed magnetic field and by disturbance of the field by a flaw represents a sufficient change to signal the detection of a flaw. This signal can be in the form of an audible signal that can be heard or a visual signal that can be printed out in the form of a graph. Also is desired, the flaw detection signal may activate marking equipment that causes the workpiece to be appropriately marked in the area of the flaw. Moreover, the changes in the magnetic field can be calibrated for accurate measurements of the defect.

In addition to means for detection of longitudinal flaws in the workpiece, the housing may also be provided with an additional essentially static magnet support structure through which the workpiece passes during an inspection operation. A plurality of magnet support shoes are arranged with coil-containing pads oriented in generally transverse relation with the workpiece, and each magnet support shoe supports a magnet assembly that is arranged with horseshoe-type magnets disposed with the extremeties thereof in substantially parallel relationship with the axis of the workpiece. In this case an elongated coil is located within a coin-containing pad, with the coil being oriented substantially transverse to the longitudinal axis of the workpiece. The magnet elements are arranged to generate a small localized magnetic field within the wall structure of the workpiece that is of elongated nature with the length disposed transversely to the axis of the workpiece and with the lines of flux of the magnetic field defining planes that substantially parallel the axis of the workpiece. During inspection operation the transverse elongated magnetic field is severely disturbed when interrupted by a transverse flaw in the metal structure of the workpiece. If the workpiece is of circular cross-section, such as when tubing or other pipe is being inspected, the coil-containing pads will be of curved configuration in order to conform to the configuration of the outer periphery of the workpiece. Each of the magnet and coil assemblies is arranged in overlapping staggered relationship so that the entire peripheral surface of the workpiece is interrupted by one or more magnetic fields as the workpiece is moved linearly relatively to the transverse and longitudinal flaw detection apparatus at the inspection station. The transverse magnet and coil assemblies are each carried by movable shoe elements that enable the coil-containing pads to have contact with the surface of the workpiece during the inspection operation. As enlargements, unevenness, etc., are encountered during inspection of the workpiece, the magnet-carrying shoe elements will shift to accommodate differences in dimension and yet maintain the coil-containing pad elements in positive engagement with the outer periphery of the workpiece at all times.

An AC induction coil may also be positioned at the inspection site, and the elongated workpiece being tested may be passed through the induction coil for the purpose of detecting any abnormalities in the quality of the material from which the workpiece is formed and for detecting any abnormalities in the wall thickness of the workpiece during the same inspection for flaw detection.

BRIEF DESCRIPTION OF THE DRAWINGS

So that the manner in which the above-recited features, advantages and objects of the present invention, as well as others which will become apparent, are attained and can be understood in detail, more particular description of the invention, briefly summarized above, may be had by reference to the embodiments thereof which are illustrated in the appended drawings, which drawings form a part of this specification.

It is to be noted, however, that the appended drawings illustrate only typical embodiments of the invention and are therefore not to be considered limiting of its scope, for the invention may admit to other equally effective embodiments.

In the drawings:

The present invention, both as to its organization and manner of operation may best be understood by way of illustration and example of certain embodiments, when taken in conjunction with the accompanying drawings in which:

FIG. 1 is a plan view of an inspection station illustrating joints of tubing, drill stem or the like being passed through apparatus constructed in accordance with the present invention for detecting longitudinal and/or transverse flaws in the material of the tubing, and also for detecting any abnormalities in the material from which the workpiece is composed. FIG. 1 also illustrates in schematic form the electronic circuitry and recorder for identifying flaws in any particular ones of the workpieces.

FIG. 2 is an enlarged, more detailed elevational view of a preferred embodiment of the present invention wherein magnetic detection apparatus is provided for detection of longitudinal flaws in workpieces and for detection of abnormalities in the material from which the workpiece is formed.

Figure 3A:
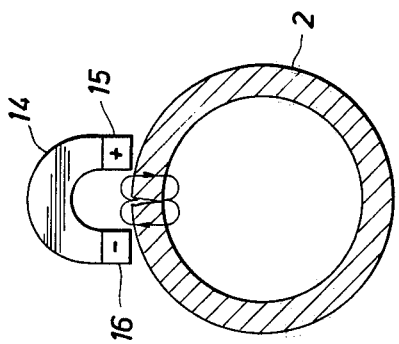

FIG. 3A is a transverse sectional view of a workpiece with a magnet oriented in juxtaposed relation thereto and illustrating the development of a small localized magnetic field within a particular portion of the workpiece.

Figure 3B:
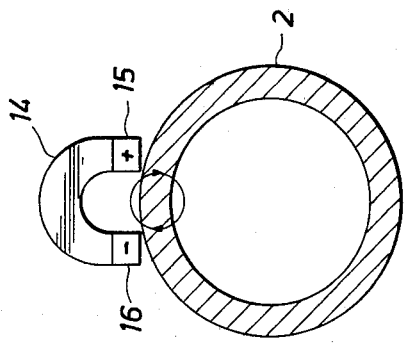

FIG. 3B is a transverse sectional view similar to FIG. 3A and illustrating modification of the form of the magnetic field when it is interrupted by a longitudinal flaw in the workpiece being inspected.

Figure 4:
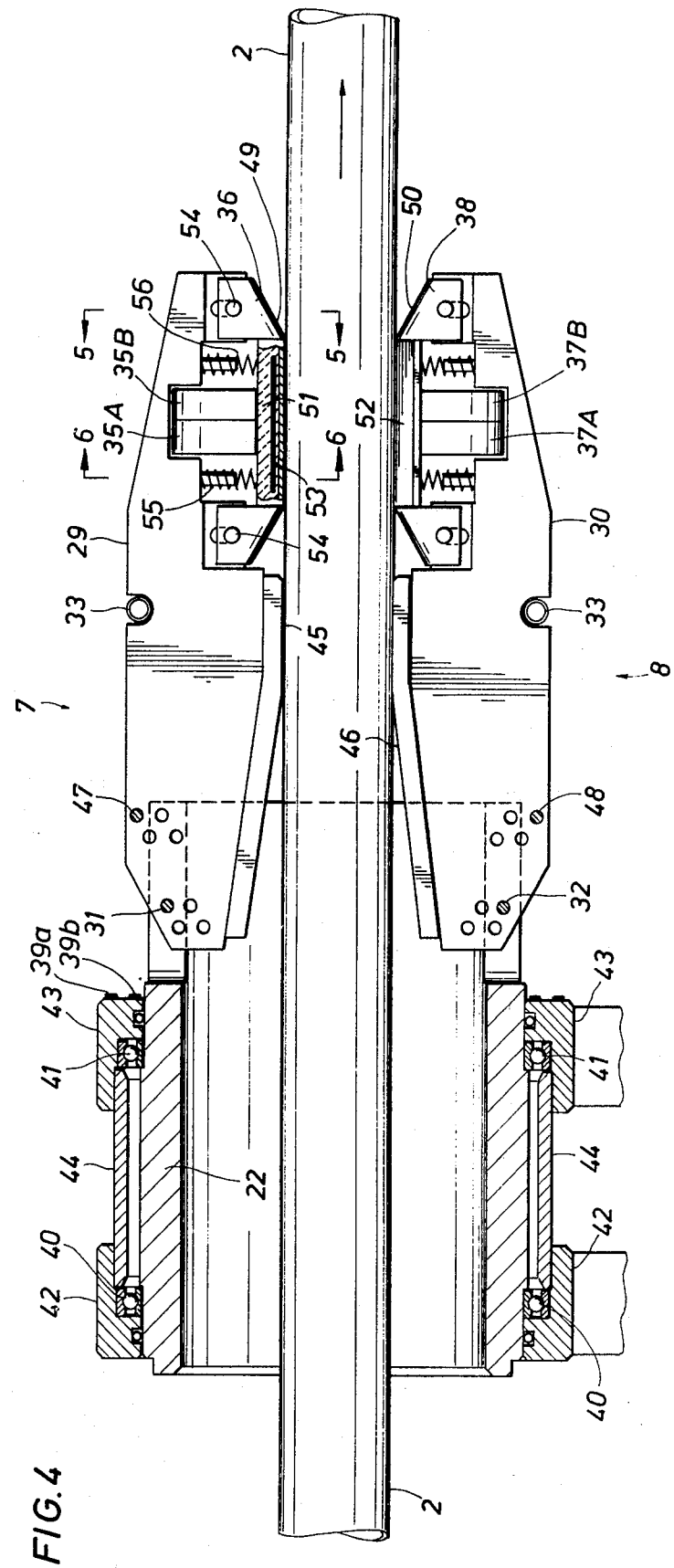

FIG. 4 is a sectional view of the rotary head portion of the apparatus illustrated in FIG. 2, with the rotary head structure and the magnet shoe support structure being illustrated in detail.

Figure 5:
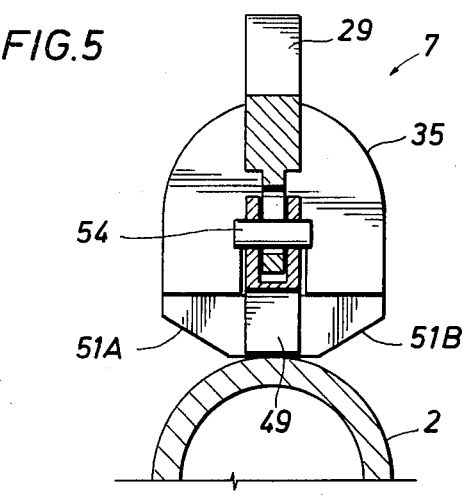

FIG. 5 is a transverse half-sectional view taken along line 5—5 in FIG. 4 and illustrating the magnet and magnet support structure of the testing apparatus in detail.

Figure 6:
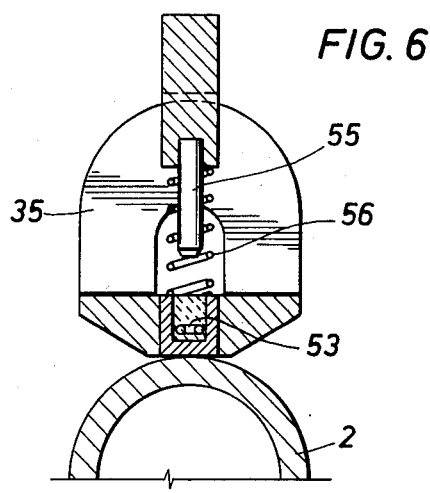

FIG. 6 is a transverse half-sectional view taken along line 6—6 in FIG. 4 and illustrating the magnet shoe guide structure and coil structure thereof in detail.

Figure 7:
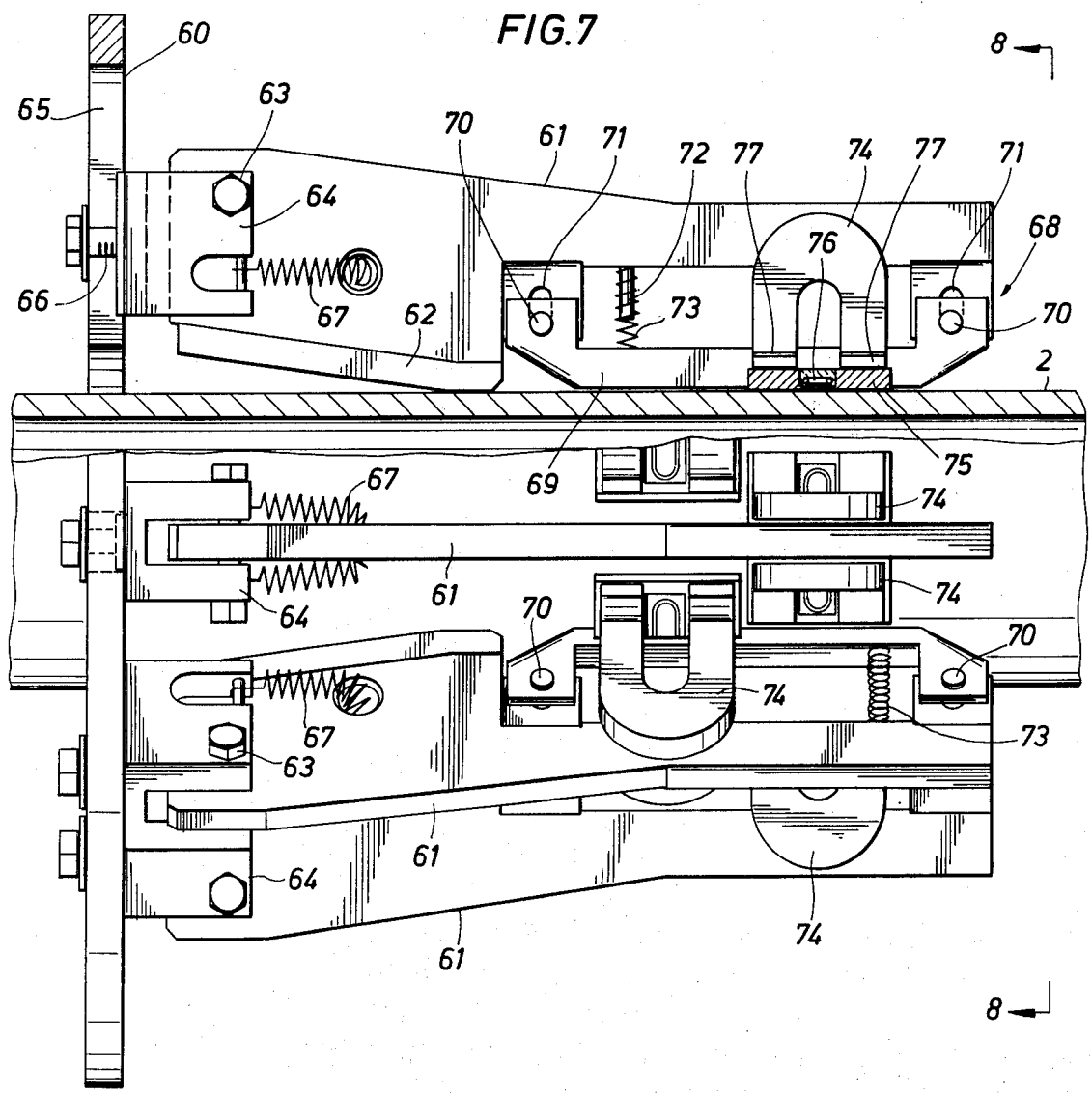

FIG. 7 is an elevational view with parts thereof broken away and shown in section illustrating magnet support head structure for detecting transverse flaws in the workpiece being tested.

Figure 8:
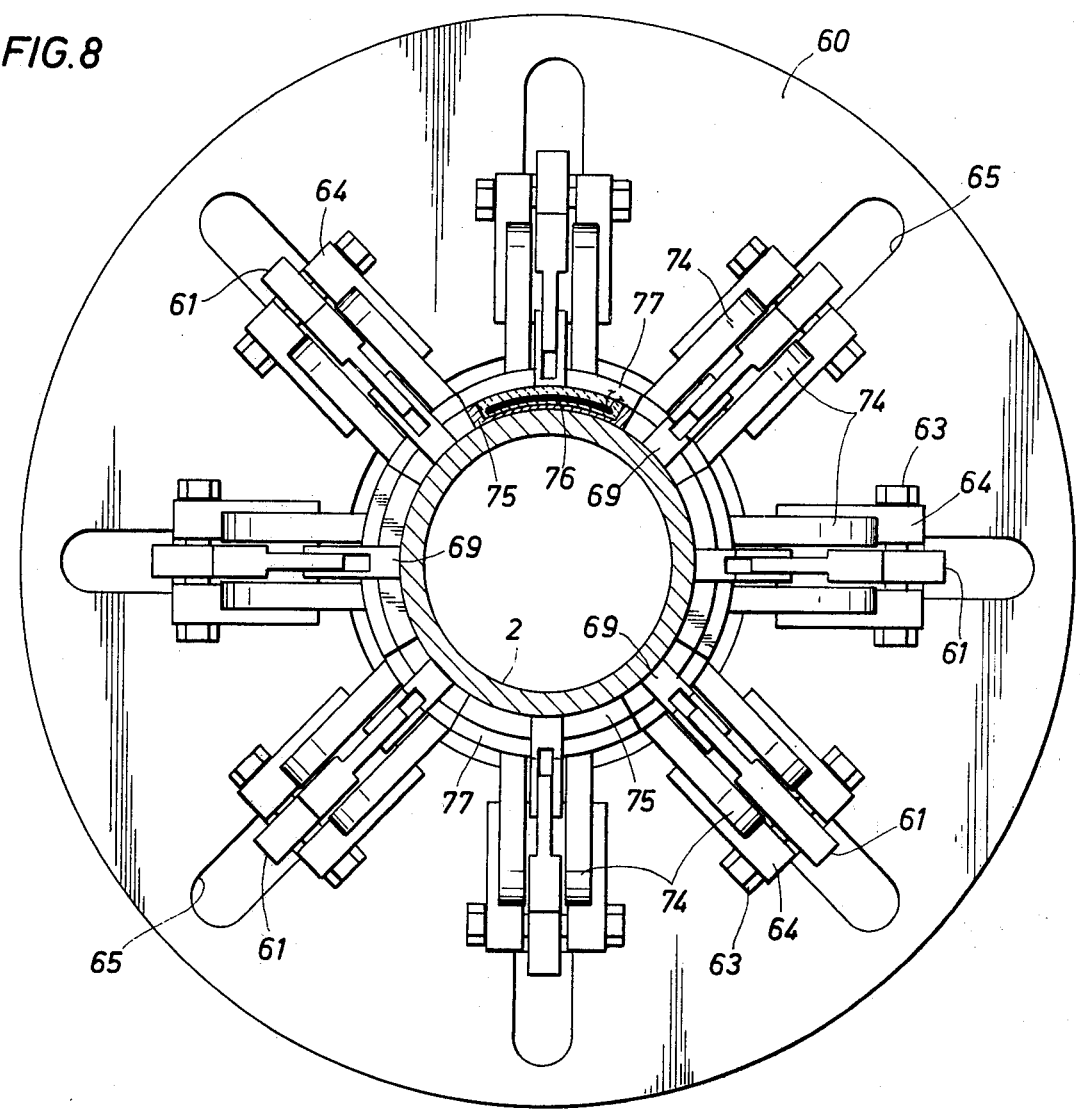

FIG. 8 is an elevational view taken along line 8—8 in FIG. 7 and illustrating the relationship of the various magnet support shoe assemblies and their respective relationship to a pipe that is shown in section.

Figure 9:
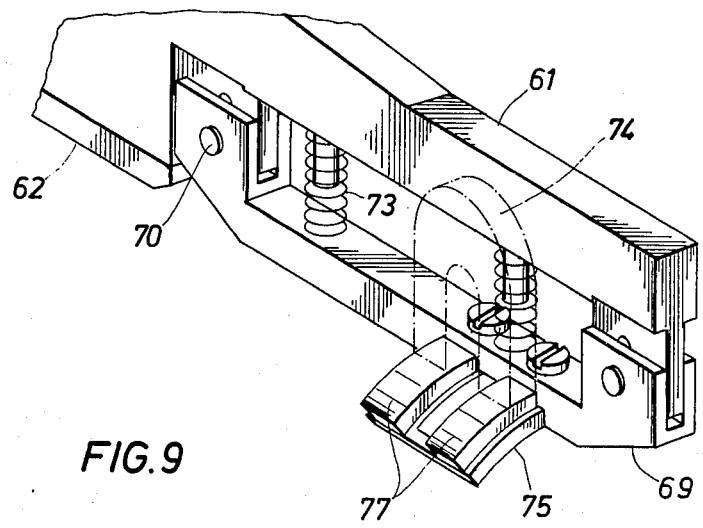

FIG. 9 is a fragmentary isometric view illustrating one of the magnet support shoe assemblies for detection of transverse flaws and showing in broken line the particular position of one of the magnets relative to the shoe and shoe support structure.

FIG. 10 is a partial elevational view of non-destructive testing apparatus representing a modified embodiment of the present invention wherein testing apparatus is provided for detection of both longitudinal and transverse flaws in workpieces.

FIG. 11 is a sectional view taken along line 11—11 in FIG. 10 and showing the position of the various magnet support head structures of the apparatus illustrated in FIG. 10 relative to the workpiece being inspected.

FIG. 12 is an electronic schematic illustration showing the various coil devices of the testing apparatus and illustrating amplification and display circuitry for processing the electric signals that are generated in the various coils.

FIG. 13 is a schematic illustration illustrating the relationship of a power supply and time switch mechanism to magnet and coil assemblies capable of detecting both longitudinal and transverse flaws in workpieces.

FIG. 14 is an electrical schematic illustration of electrical circuitry that is capable of detecting changes in the hardness of the material from which a workpiece is formed, hardness testing being accomplished simultaneously with detection of flaws in a material from which the workpiece is made.

FIG. 15 depicts a galvanometer module that is capable of recording in graphical form the hardness characteristics as well as metal flaw characteristics of the particular workpiece being tested.

FIG. 16 is a view taken along line 16—16 of FIG. 15 and illustrating the mounting board structure of the galvanometer assembly in full line, while showing the enclosure for the galvanometer assembly in broken line.

FIG. 17 is a view illustrating assembly of a number of recording galvanometers, showing in broken line the assembly of other galvanometer modules to accommodate additional testing circuits for the non-destructive testing mechanism of the present invention.

DESCRIPTION OF PREFERRED EMBODIMENTS

Referring now to the drawings, and first to FIG. 1, there is shown a pipe 2 to be tested, which pipe may be obtained from a pipe supply shown at the left portion of FIG. 1 and may be passed from left to right through the flaw and material hardness testing apparatus. The pipe 2 may then be received by appropriate pipe-receiving apparatus such as shown at the right-hand portion of FIG. 1. For the purpose of detecting flaws and material hardness of the pipe or tubing 2, there may be provided workpiece examining apparatus, such as shown generally at 3, which includes an AC induction coil 4 that is positioned in fixed relation at the inspection station. The examining apparatus 3 may also include a pair of transverse flaw detection shoes 5 and 6 that may be supported at one extremity of the examining apparatus and a pair of longitudinal flaw detection shoes 7 and 8 and may be carried at the opposite extremity thereof.

It is considered desirable to cause the longitudinal flaw detection shoes carried by the examining apparatus to traverse the entire surface area of the elongated workpiece being tested. One suitable means for accomplishing this purpose may conveniently take the form of a rotating head assembly 9 that supports a pair of balancing shoes 10 that are disposed in 90° offset relationship to the longitudinal detection shoes 7 and 8. To provide meaningful data processing relating to the material hardness and flaw detection testing apparatus, there will be provided suitable electronic circuitry and recording circuitry such as illustrated at 11 in FIG. 1.

For the purpose of detecting longitudinal flaws in the respective workpieces, the theory of operation of the testing apparatus of the present invention may conveniently take the form illustrated in FIGS. 3A and 3B where a small localized magnetic field is shown to be developed in a portion of the workpiece 2 by means of a magnet 14 having cores 15 and 16. The magnetic field is shown by a small circle as in FIG. 3A with arrows pointing to the direction of flux that is induced into the material of the workpiece.

As illustrated in FIG. 3B, the magnetic field, shown in its undisturbed condition in FIG. 3A is drastically modified as shown by FIG. 3B when a longitudinal fissure interrupts the magnetic field. As the workpiece is rotated relative to the magnet, the magnetic field, upon being interrupted by a flaw in the workpiece, will become modified, thus inducing a change in the electrical signal that is responsive to the magnetic field. The change in the electrical signal being developed can be utilized in any suitable fashion to provide an indication that a flaw has been detected.

Referring now to FIG. 2, there is shown a roller rack 20 having a pair of spaced rollers that receive the workpiece 2 and provide for substantially horizontal movement of the workpiece through the inspection station at which the flaw and material hardness testing apparatus is located. Between the spaced rollers and connected to the roller rack framework may be provided a centering jack 21 that provides support for a mounting ring 22 that may be rotatably driven by means of an electric motor 23 through a suitable gear reduction 24. The output shaft 25 of the gear reduction 24 may be provided with a sprocket that receives a sprocket chain, which chain is also received by a drive sprocket 27. An electrical cable 28 is suitably connected to a control signal junction box and to the recording portion of the electronic circuitry 11. The cable 28 may be provided with any suitable number of conductors, each of which relates to the particular electrical signal that is generated by any one of the number of magnetic detection devices with which the testing apparatus is provided.

The mounting ring 22 may provide movable support for a plurality of shoe pivot arms 29 and 30 that may be pivotally connected to the mounting ring 22 by means of pivot pins 31 and 32.

Because the shoe pivot arms 29 and 30 are urged toward the workpiece being tested, thereby causing the respective shoes to be maintained in engagement with the workpiece, a tension spring 33 may be received within appropriate recesses or grooves formed in the respective shoe pivot arms, thereby providing a continuous force that acts upon the arms to urge them radially inwardly. On either side of the respective shoe pivot arms 29 and 30, there may be provided a pair of balancing arms 34 that are also engaged by the tension spring 33 to cause the tension spring 33 to provide balanced urging forces acting upon the arms 29 and 30. The balancing arms 34 prevent the spring from coming into contact with the workpiece 2 as it is passed through the inspection station. Each of the arms 7 and 8 may be provided with shoe assemblies 36 and 38, respectively, with magnets 35 and 37 being supported by each of the shoe assemblies. The magnets carried by each of the shoe assemblies are positioned by the shoe assemblies relative to the workpiece such that small localized magnetic fields are induced into the workpiece as shown in FIG. 3A. The nature of each of the magnetic fields of each of the shoe assemblies is detected electrically by means of a coil to be discussed in detail hereinbelow, and electrical signals from the various coils may be conducted to circular contactor means provided on the mounting ring 22. A brush assembly 39 may be utilized to pick up the electrical signals from the circular contactor because of the rotary relationship between the mounting ring and the mounting ring support structure.

For the purpose of providing for rotation of the magnet support shoe assemblies carried by the respective arms 7 and 8, the mounting ring assembly 22 will have rotatable relationship relative to a housing support structure. Bearing assemblies 40 and 41 may be provided that are received within appropriate recesses formed in bearing holders 42 and 43, with an appropriate sleeve 44 being interposed between the hearing holders to maintain an appropriately spaced relationship therebetween and to provide for sealing of the bearing structures against contamination by dust, dirt, water and the like.

Each of the support arm assemblies 7 and 8 may be provided with respective wear bars 45 and 46 that are composed of any suitable wear-resisting material and which are secured to the respective arms in any suitable manner. The wear bars 45 and 46 will have engagement with the outer periphery of the tubular workpiece to be tested, and will thereby properly position the respective arms, and thus the shoe assemblies carried by the arms, relative to the workpiece. When a workpiece is not positioned between the arms, stop pins 47 and 48 carried by the arms will engage stop structure on the mounting ring, thus limiting radially inward movement of the arms. A number of adjustment apertures are provided in each of the arms in order that both the pivotal relationship of the arms relative to the rotary mounting ring and positioning of the arms in the absence of the presence of a workpiece therebetween can be appropriately adjusted as suits the particular characteristics of the inspection operation.

Each of the shoe assemblies may be provided with brackets 49 and 50, respectively, that provide supports for cores 51 and 52, which cores will be composed of any nonmagnetic material such as brass or aluminum or any one of a number of suitable plastic materials. Within each of the cores may be located electric coils such as shown at 53 that are located between the magnets 35A and 35B, as well as magnets 37A and 37B, for the purpose of detecting the characteristics of the magnetic flux developed in the material by the magnets. The coils are electrically connected in any suitable manner to the contact ring in order that electrical signals induced into the coils may be detected by means of the brush assembly 39 that contacts collector rings 39a and 39b which are connected to, but insulated from, the bearing holder 43. Each of the brush assemblies may be provided with retainer pins 54 that are received within elongated slots defined in the respective pivot arms 29 and 30. The interrelationship between the retainer pins 54 and the respective elongated slots allows the magnet support shoes 36 and 38 to have linear movement relative to the respective arms within limits defined by the length of the slots, but prevents the magnet shoe assemblies from becoming disassembled from the arms in absence of contact with the surface of a workpiece. Linear movement of the respective shoes relative to the arms 29 and 30 may also be controlled by means of guide pins 55 that receive compression springs 56. The compression springs cause the shoes to be urged into engagement with the peripheral surface of the workpiece, and the pins 55 serve as retainer elements for the springs as well as controlling linear movement of the shoes.

The coil, guide pin and spring are clearly evident from the transverse sectional views 5 and 6. Reference characters 51A and 51B depict pole pieces that are composed of magnetic material, such as soft iron, that serve to support the free extremities of the horseshoe-type magnets 35 to establish proper positioning of the magnets relative to the workpiece being inspected. The primary purpose of the pole pieces is to disperse the magnetic field on each side of the coil 53. As shown in FIG. 6, the cores that retain the electrical coil elements may be of elongated configuration and composed of a non-magnetic material, such as aluminum, brass, etc., with an elongation trough or receptacle being defined within the core structure. After the coil 53 has been properly positioned within the elongated trough or core receptacle, a quantity of plastic material may be poured into the trough, submerging the coil, and, after curing, will encapsulate the coil and cause it to be positively retained in position within the core.

Referring now to FIG. 4, in the absence of a workpiece, the arms 29 and 30 will be collapsed by the tension spring 33 within limits allowed by the stop pins 47 and 48 which engage the rotary mounting ring 22. Upon feeding of a workpiece through the testing apparatus in the direction shown by the arrow at the right-hand portion of FIG. 4, the workpiece will engage the angulated portion of the wear bars 45 and 46 and will provide sufficient force to overcome the tension of the spring 33, thereby causing the arms to move to the position illustrated in FIG. 4. As the workpiece moves further, the extremity of the workpiece contacts the angulated portion of the respective magnet support shoes, thereby causing a camming action that moves the shoes linearly, causing the pins 54 to travel linearly within the slots provided therefor. The compression springs 56 about the guide pins 55 will continuously urge the shoes toward the workpieces and will maintain contact between the workpieces and the shoes during testing operations, thereby positively maintaining proper positioning between the magnets and the workpieces to ensure consistency of the electrical signal that is transmitted to the contact or collector rings 39A and 39B. The wear bars 45 and 46 provide appropriate support for the arms 29 and 30 during testing operations by virtue of engagement with the workpiece being tested. This causes the shoes 36 and 38 to be subjected only to the degree of force that is induced by the compression springs 56, thereby precluding unnecessary wear on the core portions of the shoe structures during testing operations.

Referring now to FIG. 7, there is disclosed a modified embodiment of the present invention that is provided for detection of transverse flaws in the workpiece being tested. If desired, the structure illustrated in FIG. 7 may be secured at the inspection site and may be used simultaneously with the apparatus disclosed in FIGS. 1–6 for detection of longitudinal flaws. As shown in FIG. 7, there is provided a mounting plate structure 60 having a plurality of pivot blocks 64 connected thereto by means of adjustment bolts 66 or by any other suitable means of connection. The pivot blocks 64 each provide pivotal support for a transverse flaw detector arm assembly, such as shown at 61, which is also provided with a wear bar 62 that engages the pipe or tubing 2 during the inspection operation and thereby serves to position the respective arms 61 relative to the workpiece. Connection between the arms 61 and the respective pivot blocks 64 may be accomplished by means of pivot pins 63 which may be in the form of ordinary bolts that extend through apertures formed in each of the arms 61. For the purpose of adjustment, the attachment and adjustment bolts 66 that secure the pivot blocks 64 to the mounting plate 60 may extend through elongated slots 65. After loosening of the adjustment bolts 66, the arms may be suitably positioned within limits defined by the elongated slots 65, thereby allowing the inspection apparatus to be readily adjusted to accommodate different size tubing or pipe.

It will be desirable to cause the arms 61 to be urged toward the workpiece being inspected, and for accomplishment of this purpose, tension springs 67 may be extended through spring openings formed in the respective arm structures 61 with the extremities of the springs being secured to spring-retainer posts that are carried by the respective pivot blocks. Because the springs are offset relative to the pivot established by pivot element 63, the tension springs will induce a force to the respective arms, tending to pivot the arms toward the workpiece that is being tested.

The respective arms 61 will be formed to define recesses for receiving magnet and coil-supporting shoe assemblies and may also define shoe assembly support elements, each having an elongated slot 71 formed therein with retainer pins 70 received within each of the elongated slots 71 which serve to retain shoe bracket structures 69 in movable, but retained, assembly with the arm structure 61. The shoe assemblies 68 may each include the bracket structure 69, and the bracket structure, together with the magnet and coil assembly carried thereby, will be guided during linear movement within the shoe-retaining recess by means of guide elements 72 and will be urged toward the workpiece 2 by means of a compression spring 73 that is received about each of the guide elements.

Each of the brackets 69 of the shoe assembly 68 will be provided for support of at least one, and preferably a pair, of horseshoe-shaped magnets 74, with the free extremities of each magnet being supported by magnetic pole pieces 77 that may be composed of soft iron and by non-magnetic shoe structure 75 that, for practical purposes, may be composed of brass or any other suitable non-magnetic material. The non-magnetic shoe structure 75 may be formed to define an elongated coil-retaining recess within which may be positioned an electrical coil 76 that is capable of detecting the magnetic field being induced into the workpiece by each of the magnets. The soft iron pole pieces 77 may be interposed between the free extremities of each of the magnets 74 and the brass shoe to establish a connection therebetween. The coil 76 may be retained within its recess by means of a non-magnetic material, such as plastic, that may be poured into the recess in an uncured state and allowed to cure into a relatively solid substance.

As illustrated in FIG. 9, each of the iron pole pieces 77 and the non-magnetic shoes 75 are of curved configuration, conforming to the configuration of the workpiece being tested. Additionally, the non-magnetic shoes and the pole pieces extend outwardly beyond the respective magnets, causing the magnetic field that is generated through the pole pieces and into the workpiece to be of elongated configuration when viewed transversely of the workpiece. The lines of force of the magnetic field, however, are in line with the axis of the workpiece and transverse to the coil.

As is evident from FIG. 7, the various magnet support shoes are staggered such that the magnetic fields generated thereby are disposed in overlapping relationship such that the entire peripheral surface area of the workpiece is subjected to the overlapping magnetic fields as the workpieces have moved relative to the arm and shoe assemblies 68. A single pass of the workpiece through the magnetic flaw detection apparatus illustrated in FIG. 7 will cause the entire surface area of the workpiece to be inspected, and, upon detection of a transverse flaw in the metal structure of the workpiece, a signal will be generated that can be audibly or visually displayed to indicate that the workpiece is defective. Moreover, the structure illustrated in FIG. 7 may be utilized separately from, or in conjunction with, the magnetic testing apparatus illustrated in FIGS. 1–6, depending upon the characteristics of inspection that are desired. Since the entire surface area of the workpiece is inspected simply by passing the workpiece through the apparatus illustrated in FIG. 7, it is not necessary to rotate the transverse flaw detection apparatus during the testing operation. Therefore, only the magnetic detection apparatus illustrated in FIGS. 1–6 need be rotated, and the transverse flaw detection apparatus may simply be maintained in a stable condition as testing operations are being conducted.

It may be desirable to provide magnetic flaw detection apparatus that is constructed in accordance with the present invention and is capable of detecting both longitudinal and transverse flaws in the workpiece during a single inspection pass. It may also be desirable to cause rotation of both the transverse and longitudinal detection apparatus to provide a helically movable relationship with the workpiece that causes the entire surface area of the workpiece to be inspected during a single inspection pass. In accordance with the present invention, such apparatus may conveniently take the form illustrated in FIG. 10, where a pair of longitudinal flaw detection arms 80 are shown to be connected to a rotary mounting ring 84 that may be rotated in any suitable manner. Each of the longitudinal flaw detector arms 80 will be formed with an appropriate recess to receive respective shoe assemblies 83 that are linearly movable relative to the respective arm in the same manner as discussed above in connection with FIG. 4. The longitudinal flaw detection shoe assemblies may take a similar or identical form as compared with the shoe assemblies 36 and 38 shown in FIG. 4. Magnets 81 and 82 may be supported by each of the shoe assemblies and may be positioned relative to the workpiece so as to induce into the workpiece a small localized magnetic field that is oriented relative to the workpiece, with the lines of flux thereof being oriented transversely of the longitudinal axis of the workpiece. As in the structure of FIG. 4, the shoe assembly also includes an electrical coil that is retained by the shoe assembly and is positioned in the magnetic field between the magnet and the workpiece.

In addition to the longitudinal flaw detector magnet and coil assemblies, there may be provided a pair of opposed transverse flaw detector arms 85, each of which is oriented in substantially 90° relationship to each of the longitudinal flaw detector arms 80.

Referring particularly to FIG. 11, the arms 85 will be formed to define shoe-receiving recesses capable of retaining transverse flaw detection shoes such as shown generally at 85A and 85B. Each of the transverse flaw detection shoes may conveniently take the form of the shoe assembly structures illustrated in FIG. 7 with non-magnetic shoe plates that are curved to conform to the configuration of the workpiece, which shoe may be formed with a recess within which is disposed a magnetic field detection coil that is electrically connected with suitable magnetic field signal processing apparatus, such as that shown schematically at 11 in FIG. 1. A pair of magnets 86 and 87 may be carried by the respective shoe assemblies on either side of the respective transverse flaw detector arm for the purpose of inducing a magnetic field through the respective magnetic pole pieces that are carried by each of the shoe assemblies 88.

A rotating head assembly 89 will provide rotatable support for the mounting ring 84 in the same manner as discussed above in connection with FIGS. 2 and 4, thereby causing rotation of both the longitudinal flaw detector arms and the transverse flaw detector arms. As the workpiece 2 is passed through the rotatable mounting ring, the respective arms will be positioned with wear bars in engagement therewith and with shoe assemblies in floating contact with the surface of the workpiece. As the workpiece is moved linearly and the respective arms are rotated, the magnetic fields generated by the respective longitudinally and transversely oriented magnet assemblies will cause each of the magnetic fields to traverse the entire surface area of the workpiece in the form of a helical scanning path. The speed of linear movement of the workpiece and the speed of rotation of the magnetic shoe assemblies must therefore be precisely controlled in order to cause the respective magnetic fields to traverse the entire surface area of the workpiece. Detection of both longitudinal and transverse flaws in the workpiece may therefore be accomplished efficiently by means of only four magnet assemblies that are such capable of developing small localized and specifically oriented magnetic fields in the material from which the workpiece is composed.

Referring now to FIG. 12, the electrical circuitry for processing the magnetic field related electrical signals that are induced into the respective coils of the shoe assemblies is shown by means of a simple schematic illustration. In this particular case, the flaw detection apparatus would be provided with a pair of arms and shoe assemblies for detection of longitudinal flaws in the workpiece and would be provided with eight transverse flaw detection arm and shoe assemblies, such as shown in FIG. 7, for detection of transverse flaws in the metal of the workpiece. The two longitudinal flaw detection shoes carried by respective arms such as shown in FIG. 2 will provide coils 91 and 92 that provide magnetic field related signals to the input of a conventional amplifier circuit 93. The output of the amplifier circuit is then fed to a galvanometer 94 that is capable of providing a visual and/or audible signal in the event a flaw is detected by either or both of the longitudinal flaw detection shoe assemblies. A suitable galvanometer structure for providing graphical read-out of the condition of the material from which the workpiece is composed will be discussed hereinbelow in connection with FIGS. 15-17.

A plurality of coils 101 being carried one by each of the plurality of transverse flaw detection shoes such as shown in FIG. 7 will provide electrical signals to the input of respective amplifier circuits 102. The output of each of the amplifier circuits will then be fed to recording or audible signal-generating galvanometer assemblies, such as shown at 103.

Referring now to FIG. 13, it may be desirable to provide electrical or electronic apparatus for obtaining and processing electrical signals on a time-sharing basis in order to utilize more simple and efficient electrical or electronic circuitry for accomplishing both longitudinal and transverse detection of flaws in the workpiece being tested. A power supply may be provided as shown at 97 that may be coupled to a time switch mechanism 98 that selectively connects the coils of a transverse magnetic flaw detection assembly 99 or a longitudinal flaw detection assembly 100 to be electrical signal processing circuitry. In this manner, a single power supply amplification and signal display circuit may be utilized for both transverse and longitudinal testing.

It may be desirable to test the particular characteristics such as hardness and wall thickness, of the material from which the workpiece is composed at the same time the workpiece is tested for flaws in the material structure. To provide this type of testing, an induction coil 4 may be supported at the inspection site, as shown at FIG. 2, and the workpiece 2 may be passed through it and also through the flaw detection apparatus in the manner shown in FIG. 2. There may be provided a verifier circuit, such as shown generally at 111, having a balanced bridge circuit 112 having an induction coil 113, a matching resistor 114 and a load resistor 116, to which may be coupled a power supply 115. A galvanometer 118 may be coupled to the balanced bridge circuit with one lead being connected between the induction coil 113 and the matching resistor 114 with its opposite lead forming a wiper 117 that contacts the load resistor 116. The load resistor is in the form of a variable resistor by means of the wiper 117, thereby allowing the balanced bridge circuit to be balanced simply by adjustment of the position of the wiper 117 relative to the variable load resistor 116. A threshold circuit 119 may also be connected across the galvanometer 118 and may establish a predetermined threshold beyond which a particular signal may be given indicating that the threshold has been exceeded. Audible signal apparatus 120 may be provided in conjunction with the threshold circuit 119 and may produce a signal that is audible to the operator, such as a horn signal, that will indicate that the workpiece is not of proper hardness throughout its length. An amplifier circuit 122 may have its input connected across the galvanometer circuit and to the balanced bridge circuit with the output of the amplifier circuit being coupled to a recording galvanometer 123. A pulse generator circuit 121 may also be provided having its output connected with the amplifier circuit in order to modify the amplified signal of the amplifier circuit and feed to the galvanometer 123 an appropriate signal that may be recorded on a chart 124 by means of a galvanometer charting pin 125.

In order to provide a permanent indication of the tested condition of each particular workpiece that is tested both for hardness and for possible longitudinal and/or transverse flaws in the material thereof, a recording galvanometer for accomplishing this purpose may conveniently take the form illustrated generally at 130 in FIG. 15, where a generally horseshoe-shaped magnet 131 is provided having pole pieces 132 and 133 that may be secured to a printed circuit mounting board 134 by means of screws 128. A dust cover such as shown in broken line at 129 in FIG. 16 may be secured to the printed circuit board in any desirable manner to prevent the galvanometer assembly from becoming contaminated by dust, dirt, and the like. The printed circuit mounting board may be provided with a plug portion 135 having electrical contacts 135a for allowing the galvanometer unit assembly to be simply plugged into proper electrical contacted relationship with the electrical circuitry therefor. The printed circuit mounting board also provides structural integrity for the galvanometer assembly and allows the galvanometer assembly to be simply plugged or connected into a substantially fixed, but removable, relationship with a galvanometer receptacle where it may be assembled with other similar or identical galvanometer units, such as shown in FIG. 17.

Each galvanometer assembly may include a torsion bar 136 that is received by a torsion bar holder 137. A saddle structure 143 may also be provided that receives a center pole piece 139 about which is disposed an electrical coil 138. The coil interrupts the magnetic field between the pole pieces 132 and 133 and functions to induce a force to the saddle structure 143 that causes a pin arm 140 and pin nib 142 to assume a particular position relative to a chart, such as shown at 124 in FIG. 14. Ink from the hib 142 will provide a marking on the chart that conforms to the particular electrical signal responsive forces being applied through the center pole piece 139, the saddle 143, to the pin arm and nib. The pin arm 140 is supported by a pin arm spring 141 that causes the nib 142 to be urged into engagement with the surface of the chart 124.

A control console adapted to receive a number of galvanometer assemblies such as shown in FIGS. 15 and 16, and any number of the galvanometer assemblies, may be simply plugged into an electrically connected relationship with appropriate galvanometer actuating circuitry in the control console. As shown in FIG. 17, a number of galvanometer assemblies 130, each having pin arms 140, are disposed in side-by-side relationship with other galvanometer assemblies being shown in broken line that might be added in the event the material testing apparatus is to be provided with additional testing and recording capability. In the event one of the galvanometer assemblies of the particular testing apparatus should become inoperative for any particular reason, the testing apparatus can simply and quickly be restored to its optimum operating capability by removing the defective galvanometer module and plugging a new galvanometer module into that particular receptacle. The galvanometer apparatus can thus be repaired by workmen having little or no electrical or electronic capability. The magnet 131 may be a parmanent magnet or an electromagnet within the scope of the invention.

The same rotatable detector head structure that is rotated during longitudinal movement of the workpiece through the inspection site also provides for effective and accurate inspection of the workpiece for any dimensional changes in wall thickness that might be detrimental to use of the workpiece in service. In tubular workpieces, such as well tubing and drill stem, the hostile environment in which the pipe is used can cause corrosion and erosion of the pipe from the interior, reducing the wall thickness to the point that is should not be put to further use in wells. Means for inspecting the wall thickness of the tubing of wells may be simply and effectively accomplished in accordance with the present invention either with the tubing in place in the well or with the tubing extracted from the well and passed through the inspection apparatus in the form of sections. As the detector head, including the magnet and coil assemblies carried by the various shoes, is rotated around the pipe at a speed corresponding to the magnetic charging time of the weight and grade of material, the cross-sectional area of the pipe will be detected in the form of a flux variation, which is related to measuring instruments in the form of an electrical signal. When the body wall thickness of the pipe is relatively uniform, the electrical signal relating the flux that is detected is also correspondingly uniform. At a point in the pipe where a non-uniform area is traversed by the detector head, the magnetic field will vary substantially, and this variation will be transmitted to the measuring instruments of the control console in the form of an electrical signal that is compared with parameters of acceptance. If the signal shows the wall thickness to fall outside of these parameters, an appropriate signal will be given for the purpose of rejecting the pipe and for providing a measured indication of the characteristics of the wall thickness defect.

The signal path is a simple single channel originating at the detector head. The flux path is directly opposite to the transverse detection system. As the detector head is passed over the defect, a voltage change caused by the flux change is amplified and then presented as an amplitude change on a strip recorder for permanent records and evaluation. The recorder can be calibrated with a known standard in order to insure accurate measurements of the wall thickness of the tubing.

The magnetic field is induced into the pipe at the detector head and is so designed that it is an integral part of the detector head. This method insures that a uniform magnetic field is present at the point of detection. Extremely accurate wall thickness measurements are possible in accordance with the teachings of this invention.

While discussion of wall thickness measurement has been limited to exterior application of the measuring apparatus to pipe, it is not intended that this form of discussing the nature and scope of the invention limit the invention in any way. For testing tubing strings in place within wells, the same inventive concept may be effectively employed by passing a well tool through the tubing string, with detecting head structure incorporated into the well tool and having the capability of wiping along the inside wall surfaces of the tubing and detecting any abnormalities in the wall thickness of the tubing.

In view of the foregoing, it is easily seen that this invention is one well adapted to attain all of the features and advantages hereinabove set forth, together with other features and advantages which will become obvious and inherent from a description of the apparatus itself. It will be understood that certain combinations and sub-combinations are of utility and may be employed without reference to other features and sub-combinations. This is contemplated by, and is within the scope of, the present invention.

What is claimed is:

1. Mechanism for detecting the presence and location of an imperfection in an elongated ferrous workpiece, comprising magnet means for establishing a first localized magnetic field which is extremely small relative to the workpiece as a whole and which is restricted to only a portion of said workpiece and of a size expected to contain the imperfection sought to be detected, means for moving said first localized magnetic field relative to said workpiece and to said imperfection to create a distortion in said field which is functionally proportional to said imperfection and which is large relative to the size of said field, coil means for generating a first electric current responsive and proportional to said distortion resulting from the presence of said imperfection in said first localized field, second magnet means for establishing a second localized magnetic field which is extremely small relative to the workpiece as a whole and which is restricted to only a portion of said workpiece and of a size expected to contain the imperfection sought to be detected, second means for moving said workpiece relative to said second field to create a distortion in said second field which is functionally proportional to said imperfection and which is large relative to the size of said second field, second coil means for generating a second electric current responsive and proportional to said distortion in said second field resulting from the presence of said imperfection in said second field, said first coil means being disposed in a direction transverse to the axis of the workpiece, said second coil means being disposed parallel to the axis of the workpiece, amplifier circuit means having the input thereof coupled to both said coil means and amplifying the electromotive force signals received at said input, signal display means being coupled to said amplifier circuit means and rendering a display that is responsive to the electrical signals received from said amplifier circuit means, said signal display means including a galvanometer mechanism capable of relating electrical signals into mechanical form, printing apparatus being connected to said galvanometer and providing a printed display of said electrical signals in graphical form, graph means being located adjacent said galvanometer and being contacted by said printing apparatus, said printing apparatus printing a graphical display of said electrical signals on said graph means, said galvanometer mechanism comprising a circuit board having an electrical circuit printed thereon and defining a plug portion, a plurality of electrical contacts being defined on said plug portion of said circuit board and being electrically connected to said printed electrical circuit, said plug portion being adapted for insertion into a galvanometer control console receptacle for connection to appropriate galvanometer actuating circuitry, a magnet being fixed to said circuit board and having a pair of spaced legs defining the poles of the magnet, a torsion bar being secured between the legs of said magnet, electrical coil means connected to said printed electrical circuit, said coil means being supported by said torsion bar and being rotated against the restraining force of said torsion bar responsive to the electrical signal being applied to said coil, and said printing apparatus being operatively connected to said coil means for movement in response to said electrical signal and being positioned relative to print receiving apparatus by said coil means.

2. A mechanism as recited in claim 1, wherein a dust cover is connected to said galvanometer mechanism and cooperates with said circuit board to define a relatively thin and generally rectangular configuration, said galvanometer mechanism being receivable in juxtaposed relation with other similar modules to form a multiple galvanometer assembly.

3. A mechanism as recited in claim 1, wherein a control console for said galvanometer mechanism is provided for, chart means being provided at said control console and being provided with a plurality of plug-in receptacles having electrical circuit connection means, and said plug portions of a plurality of circuit boards of a plurality of galvanometer assemblies being received by said receptacles to position said galvanometer assemblies in printing position relative to said chart means, said printing apparatus being in contact with said chart means and said coil of said galvanometer being in electrical connection with the circuitry of said control console when said plug portions are received within said receptacles.

* * * * *